(12) United States Patent
Hsieh et al.

(10) Patent No.: US 10,422,768 B2
(45) Date of Patent: Sep. 24, 2019

(54) METHOD AND APPARATUS TO MEASURE ELECTROPHORETIC MOBILITY OF A FLOWING SAMPLE

(71) Applicant: Wyatt Technology Corporation, Goleta, CA (US)

(72) Inventors: Hung-Te Hsieh, Santa Barbara, CA (US); Steven P. Trainoff, Goleta, CA (US)

(73) Assignee: WYATT TECHNOLOGY CORPORATION, Goleta, CA (US)

( * ) Notice: Subject to any disclaimer, the term of this patent is extended or adjusted under 35 U.S.C. 154(b) by 35 days.

(21) Appl. No.: 15/521,255

(22) PCT Filed: Nov. 6, 2015

(86) PCT No.: PCT/US2015/059419
§ 371 (c)(1),
(2) Date: Apr. 21, 2017

(87) PCT Pub. No.: WO2016/073830
PCT Pub. Date: May 12, 2016

(65) Prior Publication Data
US 2018/0299405 A1 Oct. 18, 2018

Related U.S. Application Data

(60) Provisional application No. 62/076,366, filed on Nov. 6, 2014.

(51) Int. Cl.
*G01N 27/447* (2006.01)
*B01D 15/32* (2006.01)
(Continued)

(52) U.S. Cl.
CPC ..... *G01N 27/44721* (2013.01); *B01D 15/325* (2013.01); *B01D 15/34* (2013.01); *G01N 27/44769* (2013.01); *G01N 30/02* (2013.01)

(58) Field of Classification Search
CPC ....... G01N 27/44721; G01N 27/44769; G01N 30/02; B01D 15/34; B01D 15/325
See application file for complete search history.

(56) References Cited

U.S. PATENT DOCUMENTS

| 5,429,728 A | 7/1995 | Gordon |
| 8,525,991 B2 | 9/2013 | Hsieh et al. |

(Continued)

OTHER PUBLICATIONS

Lee, et.al., "Real-Time measurement of electroosmotic flow in capillary zone electrophoresis," Analytical Chemistry, V. 66, No. 17, 1994, pp. 2694-2700, American Chemical Society, US.

(Continued)

*Primary Examiner* — J. Christopher Ball
(74) *Attorney, Agent, or Firm* — Leonard T. Guzman

(57) ABSTRACT

When measuring electrophoretic mobility it is customary to apply an electric field and determine the electrophoretic velocity while minimizing all other contributions to the particle movement. A method and apparatus for the measurement of mobility while the sample is flowing is disclosed. Combined with a fractionation system, this approach further enables the direct measurement of individual species' mobility within a multi-modal sample. Other advantages of this new mobility measurement approach include the ability to easily pressurize the sample to suppress electrolysis, mitigation of oxidation-reduction effects and efficient heat dissipation.

9 Claims, 3 Drawing Sheets

(51) Int. Cl.
   *B01D 15/34*  (2006.01)
   *G01N 30/02*  (2006.01)

(56) References Cited

U.S. PATENT DOCUMENTS

| | | |
|---|---|---|
| 9,335,250 B2 | 5/2016 | Trainoff |
| 2011/0186434 A1 | 8/2011 | Naumann et al. |
| 2011/0210002 A1 | 9/2011 | Hsieh et al. |
| 2014/0027286 A1* | 1/2014 | Ikegami .......... G01N 27/44721 204/549 |

OTHER PUBLICATIONS

Wyatt Technology Corporation, "Möbiuz," promotional literature, 2013, Santa Barbara, US.

\* cited by examiner

METHOD AND APPARATUS TO MEASURE ELECTROPHORETIC MOBILITY OF A FLOWING SAMPLE

BACKGROUND

The invention discloses an innovative method and apparatus by which the motion of charged particles in a solution subject to an applied electric field may be measured. Although the present invention will refer to macromolecules throughout much of its specification, the invention includes more generally all classes of small particles including emulsions, viruses, nanoparticles, liposomes, macro-ions and any other solution constituents whose size may lie between a half and a few thousand nanometers. Thus whenever the terms "molecule," "macromolecule," or "macro-ion" are used, it should be understood they include all of the aforementioned solution-borne objects.

Electrophoretic mobility is widely accepted as a sensitive probe of interfacial charge, and it has found numerous applications in both biological and colloidal samples. The correlation between electrophoretic mobility and colloidal stability, formulation stability and inter-molecular interactions has been and remains a subject of active research.

Electrophoresis is the migration of macro-ions under the influence of an electric field. A steady-state electrophoretic velocity, $v_e$, attained by the migrating macro-ions is linearly proportional to the applied electric field. When a field is applied, the molecules' velocities are essentially always in equilibrium. To measure electrophoretic mobility, an electric field E is applied to drive electrophoresis of charged species, whose velocity $v_e$ is then measured to determine the electrophoretic mobility through the relationship $$v_e = \mu E \quad (1)$$

where $\mu$ is the electrophoretic mobility, or the velocity per unit electric field. An objective of the present invention is to provide an improved method for the measurement of the electrophoretic mobility of particles in solution.

Several techniques have been developed and are available for measuring electrophoretic mobility. Among these techniques are the moving boundary method, microelectrophoresis, and electrophoretic light scattering, ELS, which includes several light scattering methods including heterodyne dynamic light scattering, DLS, laser Doppler electrophoresis, LDE, and phase analysis light scattering, PALS. The electrophoretic mobility can also be measured by an electroacoustic means: electrokinetic sonic amplitude, ESA, as described by Oja, et.al. in U.S. Pat. No. 4,497,208, Issued Feb. 5, 1985, "Measurement of Electro-Kinetic Properties of a Solution."

Free-solution measurements of electrophoretic mobility have been routinely carried out in the batch mode wherein a sample containing macromolecules of interest is loaded into an apparatus, an AC (alternating current) electric field is applied and the electrophoretic velocity is directly measured without externally imposed flow In general, the movement of macromolecules can be diffusional, due to Brownian motion, and collective, due to electro-osmosis, electrophoresis, externally applied fluid flow, thermal convection, etc. In order to determine the electrophoretic component, the contributions to molecular motions from other mechanisms must be accounted for. The contribution from random Brownian motion is necessarily averaged out over multiple measurements. The effects of electro-osmosis can be ignored by measuring at the stationary layer, or by increasing the frequency of electric field reversal to suppress electro-osmosis. The contribution from thermal convection or residual bulk fluid flow can be subtracted out since it is independent of the direction of the applied electric field and shows up as a constant velocity component while the electrophoretic component switches polarity in synchronicity with the alternating electric field. Most instruments are able to account for thermal convection that is usually the undesirable byproduct of electrical currents. When it comes to the measurement of electrophoretic mobility, the conventional wisdom states that such measurements should be performed under minimum bulk fluid flow. A volume flow rate 0.2 mL/min or higher can easily overwhelm the mobility measurements.

A BRIEF DESCRIPTION OF THE INVENTION

In this application, we proposed an apparatus that facilitates flow-mode measurements of the electrophoretic mobility. The externally imposed flow naturally constitutes a means for introducing and extruding the sample of interest. The flow adds a constant velocity component to the macromolecular motion on top of the field-driven electrophoresis. So long as this flow velocity component is correctly subtracted out, the mobility measurement can be successfully made. We will discuss the innovative elements that make this operation possible and greatly extend the upper limit of the volume flow rate. Although PALS is taken as our primary method of measuring electrophoretic mobility and used in our illustrations, it should be understood that these innovations can be applied to other means of electrophoretic mobility measurement.

A BRIEF DESCRIPTION OF THE DRAWINGS

A DETAILED DESCRIPTION OF THE INVENTION

Figure 1:
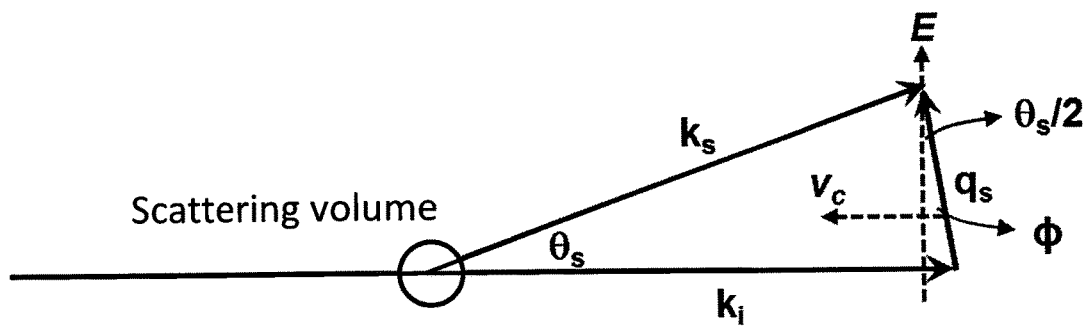
FIG. 1 shows a phase diagram for light scattering. An electric field E along the x-axis is applied to drive electrophoresis.

There are many great advantages to measuring electrophoretic mobility in the flow mode, that is while a sample flows through a measurement cell, as opposed to the batch, or stop-flow-mode, discussed previously. Among these advantages are real time, online measurement of electrophoretic mobility, constant solvent exchange mitigating the effects of oxidation/reduction reactions, pressurization of the measurement cell which can mitigate bubbles within the cell itself, and efficient heat dissipation.

The ability to resolve multiple species' electrophoretic mobilities in a given sample is often desirable. In batch-mode measurements, if the sample contains multiple species with distinct electrophoretic mobilities, the measured mobility will be some weighted average of all species' mobilities. In light scattering measurements, such as ELS, LDE or PALS, the measured mobility is the intensity-weighted average. Fourier analysis has been applied to resolve multiple mobility species in ELS, but the resolution of such multimodal analysis is limited in practice, most likely because of the inherent dual (size and mobility) polydispersity. The situation gets even more challenging when macromolecules smaller than about 20 nm are of interest, due to increased diffusional broadening in the power spectrum of the scattered signal.

Flow-mode mobility measurement can be directly coupled with numerous fractionation techniques to characterize the electrophoretic mobility of each eluted species separately. The mobility can therefore be measured "online". Size-exclusion chromatography, ion-exchange chromatography, and field-flow fractionation are just a few of the possibilities. In addition to being much more robust than numerical multimodal analyses, the on-line measurement of electrophoretic mobility provides extra information through the physiochemical parameters upon which the chemical species are fractionated. For example, size-exclusion chromatography fractionates based on the sample hydrodynamic volume. Furthermore, other sample parameters of interest, such as the concentration and hydrodynamic radius of each species, can be measured, either simultaneously or subsequently, to increase the utility of such a system. The hydrodynamic radius is a necessary parameter for the calculation of molecular charge in the Debye-Hückle-Henry model.

It is worth noting that capillary electrophoresis, CE, a well-known high-resolution separation technique, can be used for the separation of charged macromolecules based on electrophoretic mobility. In capillary zone electrophoresis, CZE, electro-osmotic flow typically dominates all electrophoretic components and all charged species are swept towards the cathode, with cations reaching the detector earlier and anions later. The electrophoretic mobility of each charged species can be computed from the time it takes for each species to reach the detector with the electro-osmotic component corrected out. To characterize the electro-osmosis, a neutral marker is necessary. However, even with a neutral marker, sample interaction with the capillary wall can never be ruled out and the measured electrophoretic mobility can be inaccurate. On the other hand, a free-solution technique is free of such non-idealities.

In addition to online mobility measurement, flow-mode mobility measurement has another interesting advantage: It mitigates the effects of reduction-oxidation, also known as redox, reactions. Mobility measurements are inherently perturbing due to the applied electric field/current. Redox reactions take place on the electrodes' surface and the macromolecular mobility can be altered either through direct modification of the macromolecular oxidation state (chemical damage) or indirect modulation by the accompanying change of buffer state (pH, ionic species, etc.). Flow-mode operation delivers a constant fresh supply of sample and buffer that greatly decreases the effects of the inevitable redox products in conductive samples.

Yet another advantage of flow-mode mobility measurement is the ease with which the measurement volume can be pressurized to avoid gas bubbles arising from electrolysis. The sample cell of a flow-mode mobility apparatus is necessarily enclosed and leak-proof up to a certain fluid pressure. A back-pressure regulator can be connected downstream from the sample cell to provide pressurization of the sample being measured. This is especially valuable when the sample contains high concentrations of salts (e.g., physiological saline) or when the gas evolution due to the ensuing electrolysis can affect the mobility measurements. Utilization of a downstream back-pressure regulator enables the sample-delivering flow to double as a means to pressurize the sample.

Passing electric current through conductive samples inevitably generates heat. Depending on the conductivity of the sample, its temperature can increase appreciably by this heat generation. An increased temperature can affect mobility measurements by changing the solution viscosity. Some degree of sample degradation can also be caused by an elevated temperature. A constant flow efficiently carries off the excess heat to maintain the temperature of the sample being measured.

It is therefore highly desirable to be able to measure electrophoretic mobility in flow-mode, yet several impediments have heretofore made any such measurements impractical. However the method and apparatus described herein allows flow-mode measurements by employing several novel enhancements to traditional systems.

To begin with, the design of the sample cell of any measurement instrument plays an important role in facilitating flow-mode measurements and achieving the full potential of the advantages. The instruments ability to properly account for the effects of a constant flow is essential to successfully measuring electrophoretic mobility in flow mode. In PALS measurements, macromolecular electrophoresis generates phase variations that are measured interferometrically to determine electrophoretic mobility, see, for example U.S. Pat. No. 8,441,638 issued May 14, 2013, by Trainoff and Hsieh, "Method and apparatus to measure particle mobility in solution with scattered and unscattered light," hereby incorporated by reference. Bulk sample flow can confound the measurements if its component along the scattering vector is excessive. As shown in FIG. 1, the sample is subjected to a flow velocity $v_c$ and an electric field E is applied to drive electrophoresis. The collective sample velocity, $v_c$, can include all collective motions which are uncorrelated with the electric field, e.g., fluid convection. Also shown are the wave vectors of the incident light, $k_i$, and the scattered light, $k_s$. The scattering vector $q_s$ is defined as $q_s = k_s - k_i$. The Doppler shift (or optical phase change per unit time) due to macromolecular electrophoresis is equal to $f_E = \mu q_s \cdot E$; this quantity is measured to determine the electrophoretic mobility $\mu$. On the other hand, the sample flow at velocity $v_c$ also generates its associated Doppler shift $f_c = q_s \cdot v_c$. Since the flow velocity $v_c$ does not change direction with the alternating electric field, the two Doppler shift components, $f_E$ and $f_c$, can in general be separated and the mobility can be determined.

However, depending on the sample electrophoretic mobility, system design and flow rate, the component $f_c = q_s \cdot v_c = q_s v_c \cos \phi$ can grow much larger than $f_E = \mu q_s \cdot E = \mu q_s E \cos(\theta_s/2)$ and start to affect the mobility measurements. A good system and flow cell design should maximize the Doppler shift $f_E$ from electrophoresis while minimizing the Doppler component $f_c$ from the fluid flow. This can be achieved by having the electric field E roughly parallel to the scattering vector $q_s$ and the collective flow direction roughly perpendicular to the scattering vector, i.e. $\phi \approx 90°$.

Figure 2:
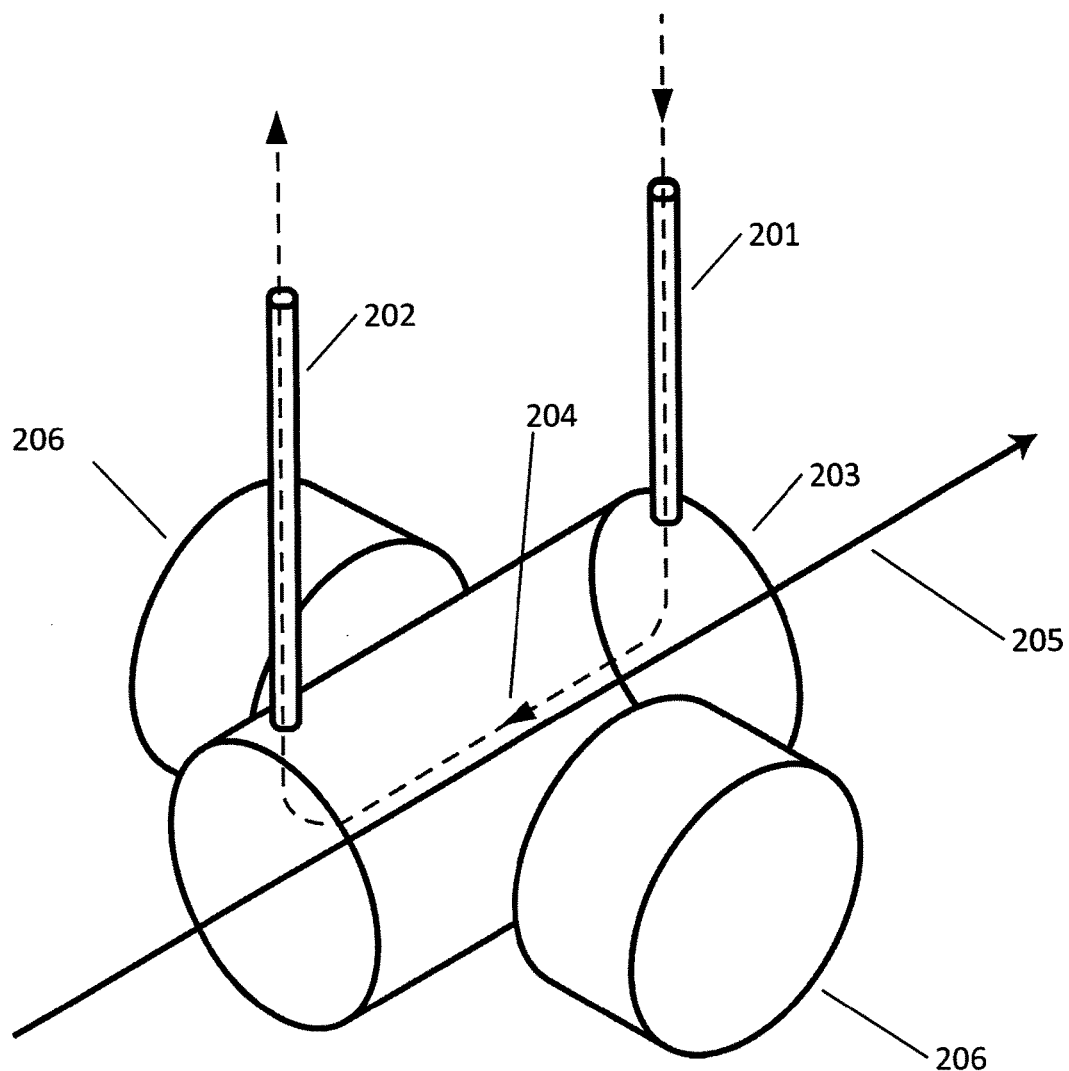
FIG. 2 illustrates the direction of fluid flow parallel to the propagation of the laser beam minimizing the associated Doppler/phase component in the low scattering angles.

FIG. 2 illustrates the elements of a specialized flow cell and assembly for measurement of electrophoretic mobility based on PALS. To minimize the component $f_c$, the fluid inlet 201 and outlet 202 of the flow cell 203 are positioned such that the fluid flow 204 direction is essentially parallel to the direction of the laser beam 205 path and perpendicular to the electric field direction generated by the electrodes 206. The flow direction is also roughly perpendicular to the scattering vector at low scattering angles of less than about 15°. With detectors covering a range of scattering angles $\theta_s$ between about 4° and 15°, the corresponding range of the angle $\phi$ is between about 88° and 82.5°. As a result the component $f_c$ is effectively suppressed, $\cos \phi \ll 1$. On the other hand, the direction of the electric field E is roughly parallel to the scattering vector $q_s$, maximizing the Doppler component $f_E$ due to electrophoresis, $\cos(\theta_s/2) \approx 1$.

The majority of the instruments for electrophoretic mobility measurements have designs wherein the electric field, scattering vector and the "would-be" flow direction are all roughly parallel to one another. Such a configuration not only renders the mobility measurements more susceptible to thermal convection effects, but also greatly limits their ability to carry out meaningful measurements when any fluid flow is present.

If a mobility measurement cell is to be used in flow mode, it is also a requirement that the sample chamber be leak-proof since the flow-mode operation is most often implemented with a fluid pump serving as means of sample delivery, and any restrictions on the fluid beyond the sample chamber itself will generate a back pressure in the measurement cell. No such requirement for the capacity to withstand significant fluid pressure is required in, for example, mobility measurement systems which make use of cuvettes. Therefore, any measurement cell designed to be used in flow mode should be leak proof, preferably capable of sustaining a back pressure of 50 bars or more.

A sample cell designed with backpressure in mind offers an additional benefit to the inventive method and apparatus disclosed herein. Such a design facilitates the pressurization of the sample chamber. The operator of the system, or the system design itself, can simply connect a back-pressure regulator at the outlet of the flow cell to apply a stable back pressure on the sample being measured. This mode of operation is especially advantageous when the sample contains high concentrations of salts such as those of physiological saline or higher. Such pressurization is also beneficial as gas evolution due to electrolysis, to which electrophoretic mobility measurements have traditionally been extremely susceptible, can adversely affect the mobility measurements.

As discussed above, the management of flow is extremely important to the successful operation of any flow-mode measurement of electrophoretic mobility. But as the flow rate increases, the flow will eventually introduce enough phase shift per unit time (i.e., Doppler frequency shift $f_c$) to confound the mobility measurement. These deleterious effects on measurement due to fluid flow begin when the actual phase shift introduced by the flow is more than $\pi$ or less than $-\pi$ between successive phase measurements. Under these circumstances, aliasing occurs and erroneous measurements of the mobility are obtained. Instruments with only one detector are especially vulnerable to this type of phase-unwrapping error because they cannot correctly detect the actual phase in this case and will "alias" the phase difference up or down modulo $2\pi$. There is no additional information available to correct for this eventuality in a single-detector mobility measurement system.

The novel solution to the problems associated with measurement of mobilities in a flowing disclosed herein comprise the utilization of multiple detectors corresponding to a range of scattering angles in the apparatus. In the absence of phase-unwrapping errors, such as, at a lower fluid flow rate, the phase shift attributable to the fluid flow, measured by the i-th detector, is the inner product $q_{si} \cdot v_c$, where $q_{si}$ is the scattering vector corresponding to the i-th detector. A global fit across all the detectors yields the fluid flow direction and velocity. In the presence of phase unwrapping errors, cross-checking the phase shifts measured by the detectors will overcome this abnormality and restore the actual phase shift to (still) accurately recover the flow direction and velocity. This greatly extends the range of usable flow rate and the instrument's capability to carry out flow-mode electrophoretic mobility measurements.

One preferred embodiment of the inventive apparatus employs 31 detectors covering arrange of scattering angles from 4° to 15°. A volume flow rate of 1.0 mL/min results in a flow velocity of approximately 10 mm/s in the center of the cell where the mobility measurements are taken. (Since the channel flow profile resembles Poiseuille flow, the average flow velocity is approximately 5 mm/s.) When the phase measurements are made at 1 kHz, phase unwrapping errors start at a flow rate of 1.0 mL/min for the highest angle. Without performing a global fit to the multiple angles, this would be the upper limit of the compatible flow rate. Note that due to the optimized flow cell of this preferred embodiment, this limit is already at least an order of magnitude higher than a conventional design where the would-be flow direction is perpendicular to the laser propagation. An upper flow rate limit of 1.0 mL/min is easily compatible with most HPLC and/or fractionation techniques. With 31 detectors, the upper limit may be extended to a flow rate beyond 40 mL/min.

Demonstration of Method

Figure 3:
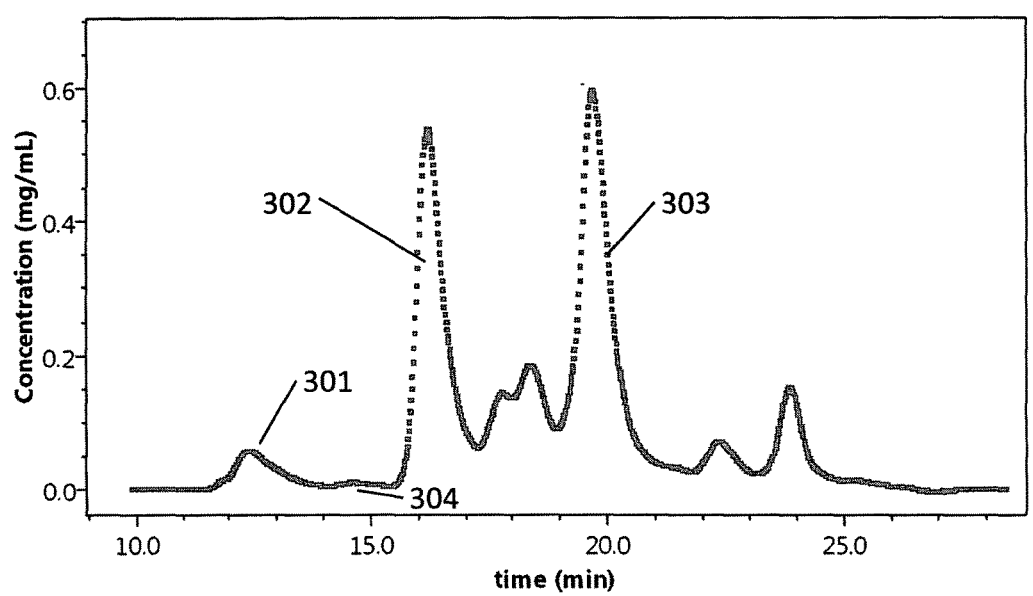
FIG. 3 shows a chromatogram of a mixture of proteins: thyroglobulin, bovine serum albumin (BSA) and carbonic anhydrase separated by SEC.

To demonstrate the feasibility of online flow-mode electrophoretic measurements as disclosed herein, the novel system is connected downstream from a size-exclusion chromatography, SEC, column with fluid flow rate passing there through of 0.2 mL/min. The sample used in this example was a mixture of three proteins, all obtained from Sigma-Aldrich, Co., St. Louis, Mo. The samples were thyroglobulin, bovine serum albumin and carbonic anhydrase. The proteins were prepared in a 10 mM sodium chloride and 10 mM phosphate buffer saline with a pH of 7.0. The same buffer served as the mobile phase of the chromatography system. The resulting chromatogram, shown in FIG. 3, was recorded by an inline refractive index, RI, detector (Optilab T-rEX, Wyatt Technology Corporation, Santa Barbara, Calif.). The three well-separated major peaks representing the monomers of the proteins are clearly seen in the chromatogram as thyroglobulin 301, bovine serum albumin 302 and carbonic anhydrase 303.

Electrophoretic mobilities of the three proteins were measured in three different ways. First a mixture of all three proteins was prepared in the buffer and measured online after passing through the SEC column. The proteins were measured again after being prepared individually in the same buffer and measured online after passing through an SEC column. Lastly, the three proteins were measured individually in the batch mode. The results are summarized in Table 1. Since the apparatus also measures the translational diffusion coefficient, the computed hydrodynamic radii are shown along with the measured electrophoretic mobilities. All averages and standard deviations are calculated based on thirty 6-second measurements. In the flow mode, we select for consideration the region of the peak which is 70% of the maximum concentration of the peak.

TABLE 1

| | Flow mode (Online) | | | | Batch Mode measurements | |
| --- | --- | --- | --- | --- | --- | --- |
| | Mixture of proteins | | Individual protein injections | | | |
| Sample | Mobility (μm · cm/V · s) | Hydrodynamic Radius (nm) | Mobility (μm · cm/V · s) | Hydrodynamic Radius (nm) | Mobility (μm · cm/V · s) | Hydrodynamic Radius (nm) |
| Thyroglobulin | −1.56 ± 0.06 | 8.70 ± 0.15 | −1.59 ± 0.10 | 8.73 ± 0.13 | −1.48 ± 0.10 | 9.40 ± 0.08 |
| Bovine Serum Albumin | −1.03 ± 0.08 | 3.48 ± 0.09 | −1.04 ± 0.09 | 3.46 ± 0.05 | −1.09 ± 0.09 | 3.56 ± 0.01 |
| Carbonic Anhydrase | −0.41 ± 0.07 | 2.42 ± 0.04 | −0.42 ± 0.09 | 2.40 ± 0.04 | −0.82 ± 0.05 | 2.64 ± 0.03 |

Note that all online measurements of electrophoretic mobility results agree well regardless of whether the proteins were injected individually or injected onto the column as a mixture. This indicates that the proteins are well separated by the chromatography system and consistently measured by the apparatus. SEC fractionates based on macromolecular hydrodynamic volume, and the measured hydrodynamic radii corroborate proper fractionation. The slight discrepancies between the batch-mode and flow-mode measurements for thyroglobulin and bovine serum albumin can be attributed to the sample polydispersity. Thyroglobulin has a monomer content of approximately 80% mass ratio and bovine serum albumin contains a 3% mass ratio of various oligomers. This can be measured by the RI detector and the oligomer peak 304 associated with the bovine serum albumin can be seen in the chromatograph of FIG. 3. The batch-mode vs. flow-mode measurements of carbonic anhydrase do not agree as well and this is most likely due to a much lower monomer content of approximately 55% mass ratio, also measured by the RI detector. The measurements of hydrodynamic radii also confirmed the sample polydispersity in the batch measurements.

The results summarized in Table 1 demonstrate the utility of flow-mode/online measurements when the bulk flow is properly accounted for. The flow-mode/online operation benefits from the fractionation method's ability to resolve multiple species in a polydisperse sample, and can achieve resolution impossible for the batch-mode operation to attain.

As will be evident to those skilled in the arts of light scattering, macromolecular characterization, and electrophoretic mobility measurements, there are many obvious variations of the methods and devices of our invention that do not depart from the fundamental elements that we have listed for their practice; all such variations are but obvious implementations of the invention described hereinbefore and are included by reference to our claims, which follow.

The invention claimed is:

1. A sample cell comprising:
   a measurement chamber configured to allow a sample solution comprising particles to flow in a direction essentially parallel to a path of a laser beam transmitted through the measurement chamber;
   a fluid inlet coupled to the measurement chamber and configured to introduce the sample solution into the measurement chamber;
   a fluid outlet coupled to the measurement chamber and configured to allow the sample solution to exit the measurement chamber; and
   electrodes configured to generate an alternating electric field across the measurement chamber and essentially perpendicular to the direction.

2. The sample cell of claim 1 further comprising a back pressure regulator configured to provide pressurization of the sample solution within the measurement chamber.

3. The sample cell of claim 2 wherein the sample cell is capable of sustaining a back pressure of greater than 50 bars.

4. A method comprising:
   flowing a sample solution comprising particles through a sample cell comprising
      a measurement chamber configured to allow the sample solution to flow in a direction essentially parallel to a path of a laser beam transmitted through the measurement chamber,
      a fluid inlet coupled to the measurement chamber and configured to introduce the sample solution into the measurement chamber, and
      a fluid outlet coupled to the measurement chamber and configured to allow the sample solution to exit the measurement chamber; and
   generating, via electrodes, an alternating electric field across the measurement chamber and essentially perpendicular to the direction.

5. The method of claim 4 further comprising applying a back pressure to the sample cell.

6. The method of claim 4 further comprising fractionating the sample solution.

7. The method of claim 6 wherein the fractionating comprises fractionating the sample solution via a field flow fractionation system.

8. The method of claim 6 wherein the fractionating comprises fractionating the sample solution via a size exclusion chromatography system.

9. The method of claim 6 wherein the fractionating comprises fractionating the sample solution via a reversed phase chromatography system.

* * * * *